United States Patent [19]

Bornstein et al.

[11] Patent Number: 5,070,243

[45] Date of Patent: Dec. 3, 1991

[54] ATTENUATED TOTAL REFLECTION SPECTROSCOPY

[75] Inventors: Aharon Bornstein, Holon; Dan Wolfman, Tel-Aviv; Mordechai Katz, Givatayim, all of Israel

[73] Assignee: The State of Israel, Atomic Energy Commission Roreq Nuclear Research Ctr., Yavne, Israel

[21] Appl. No.: 654,229

[22] Filed: Feb. 12, 1991

Related U.S. Application Data

[63] Continuation-in-part of Ser. No. 518,788, May 4, 1990, abandoned.

[30] Foreign Application Priority Data

Sep. 12, 1989 [IL] Israel .................................... 91614

[51] Int. Cl.$^5$ .............................................. G01J 3/42

[52] U.S. Cl. .............................. 250/341; 250/227.23; 356/133; 359/96

[58] Field of Search ........... 356/133; 250/341, 227.23, 250/227.31; 350/96.15

[56] References Cited

U.S. PATENT DOCUMENTS

4,654,532 3/1987 Hirschfeld ..................... 250/461.2
4,728,170 3/1988 Robertson ..................... 350/96.15

Primary Examiner—Carolyn E. Fields
Attorney, Agent, or Firm—Helfgott & Karas

[57] ABSTRACT

Method of ATR spectroscopy and substrate probe for use therein. The probe comprises a single optical fiber sensor, or a bundle of such sensors, with the sensing zone of each sensor comprising two unclad frustoconical portions merging at their frustrums.

25 Claims, 6 Drawing Sheets

ATTENUATED TOTAL REFLECTION SPECTROSCOPY

CROSS REFERENCE TO RELATED APPLICATION

This application is a continuation-in-part of application Ser. No. 518,788 filed May 4, 1990, now abandoned.

FIELD OF THE INVENTION

The present invention is in the field of optical spectroscopy. More specifically it relates to analytical spectroscopy based on measurement by the so-called Attenuated Total Reflection method which is based on the attenuation of evanescent waves propagating at the interface between an uncladded optical waveguide and a surrounding fluid medium having a lower refraction index.

BACKGROUND OF THE INVENTION AND PRIOR ART

The following prior art description outlines the background of the invention mainly in relation to infrared (IR) spectroscopy, it being understood that the present invention is also applicable in spectroscopy employing light in other ranges such as ultraviolet and visible light.

Spectroscopy is widely used nowadays in qualitative and quantitative analysis of materials. Often infrared detection techniques are advantageous over spectroscopic techniques using radiation of shorter wavelengths, such as visible light, since organic and biological materials have characteristic sharp and relatively narrow absorption peaks in the IR region.

In the performance of a direct IR spectroscopic analysis a light beam is passed across a sample material, and the transmission is measured as a function of wavelength which yields a characteristic spectrum. The measurements may be direct and yield an absorption spectrum or indirect and yield an emission spectrum.

The term "measurement" as used herein applies generally and indiscriminantly to detection, identification and quantitative measurement.

Common IR spectroscopic techniques suffer from an intrinsic problem which is due to the strong absorption of IR radiation. Because of this the substrate materials have, as a rule, to be diluted by a medium that is transparent in the infrared, e.g. a liquid such as Nujol (Trade Name) or a solid salt such as KBr. The ensuing high dilution of the sample may give rise to inaccuracies in the results.

An alternative method of direct spectroscopic measurement is the so-called Attenuated Total Reflection (ATR) method. This technique of recording the optical spectrum of a sample material uses an uncladded waveguide for the determination of the concentration of a test species dispersed in a liquid, solid or gaseous medium having a lower refractive index than the waveguide. It is based on total internal light reflection producing an evanescent light wave propagating along the waveguide/test medium interface and it measures the modulation of the evanescent light wave. The ATR technique enables to obtain accurate spectroscopic measurements with smaller amounts of sample materials than in common IR spectroscopy.

Analytical spectroscopic methods employing total internal reflection in waveguides (not ATR) are described, for example, in U.S. Pat. Nos. 4,447,546 and 4,558,014 and in WO 83/01112. These publications describe fluorimetric measurements excited by total internal reflection fluorescence techniques.

The depth of penetration of the evanescent wave into the substrate medium is strongly dependent on the incidence angle of the internally reflected light, and the closer this angle is to the critical angle (beyond which there is no total reflection), the depth of penetration increases exponentially.

The intensity of the interaction between the light travelling inside the uncladded waveguide and the medium surrounding it, is dependent on the concentration of the solution; the intensity of absorption; the depth of penetration (which itself is dependent on the incidence angle of the internally reflected light); and the number of the internal light reflections per unit length which in turn is inversely proportional to the transversal dimension of the waveguide. An increase in the number of the internal reflections amplifies linearly the interaction of the light with the surrounding substrate whereas an increase of the incidence angle amplifies the interaction exponentially.

OBJECTS OF THE INVENTION

In the following, a measuring device comprising a vessel for holding a test medium and fitted with a sensor will be referred to as "probe".

It is an object of the present invention to increase the sensitivity of spectroscopic measurements by the ATR method by intensifying the interaction between the waveguide and the surrounding test medium.

It is a further object of the invention to provide a probe with a highly sensitive optical sensor for use in the ATR method, suitable for measurements of small amounts of test materials, e.g. individual small droplets of the kind present in aerosols.

It is a still further object of the invention to provide means for direct spectroscopic measurement without need for any sensitizer reagents to mediate between the sensor and the test medium.

It is also an object of the present invention to provide a so-called dynamic probe, i.e. an effective and highly sensitive probe adapted for the continuous monitoring of a through-flowing test fluid.

It is yet another object of the present invention to provide a disposable sensitive probe for use in the ATR method, suitable for sampling a test medium, for performing an ATR analysis and, if desired, for storing the sample as reference for future measurements.

These and other objects of the invention will become apparent from the following description.

SUMMARY OF THE INVENTION

In accordance with the present invention there is provided a method of performing a spectroscopic measurement by the attenuated total reflection (ATR) method employing a tubular probe adapted to hold a substrate medium and fitted within with at least one optical fiber sensor having an unclad sensing zone, a light intake end and a light emitting end, characterised in that said unclad sensing zone of each sensor comprises two frustoconical portions merging at their frustrums.

The term "conical" as used herein means any kind of tapering configuration which may have a straight or curved generatrix.

In a probe according to the invention the two distal base portions serve for the intake and emission of light. If desired, the bases may merge into outer cylindrical portions having the same diameter as the bases and whose distal end portion provides the intake and emitting ends.

The optical fiber sensors used in the performance of the method according to the invention, may be of any suitable material conventionally used in fiberoptics such as chalcogenic compound based glass fibers, fluoridic glass fibers, silica based glass fibers and the like. The choice of the type of fiber depends, inter alia, on the range of the light spectrum at which measurements are performed.

The invention further provides for use in the performance of the above method a probe comprising a tubular casing adapted to hold a substrate medium and fitted within with at least one optical fiber sensor having an unclad sensing zone, characterised in that said unclad sensing zone of each sensor comprises two frustoconical portions merging at their frustrums.

If desired, the bases of each sensor may merge into outer cylindrical portions having the same diameter as the bases.

The tubular casing of a probe according to the invention may have a circular or polygonal cross-sectional shape.

In a sensor according to the invention, light interaction with the surrounding medium occurs along both the frustoconical portions. In consequence, the number of internal light reflections per unit length and the depth of penetration of the evanescent light wave into the surrounding medium and with it the absorption and sensitivity of a sensor according to the invention are significantly increased.

Due to the high sensitivity of the sensor(s) in a probe according to the invention there is no need for any sensitizer reagent and the test fluid can be measured directly.

Where a probe according to the invention has two or more sensors they will be referred to hereinafter as "bundle".

The signal to noise ratio of a probe according to the invention with a sensor bundle is increased as compared to a single-sensor probe due to an increase of the contact area between the sensors of the test medium and thereby an increase of the effective volume of the test medium. Such probes are useful, for example, in the continuous monitoring of test fluids such as dilute solutions, emulsions and aerosols holding small amounts of test material per unit volume.

Due to the high sensitivity of the probe according to the invention, only small quantities of test medium are required for the performance of a conclusive spectral analysis. Accordingly, in accordance with one embodiment of the invention the probe has capillary dimensions which are determined by the effective volume of penetration of the evanescent wave in the sensing zone of the sensor or sensors, as the case may be. Due to the high sensitivity of the sensors, probes according to the invention yield reliable results in real time.

A probe according to the invention may be designed for use in a batch mode of operation or for continuous use. In the batch mode the probe may serve for one-time use only and upon completion of the spectral analysis the probe with the contents may either be discarded or be stored as reference for future measurements. Due to the intrinsically small size of the probes according to the invention for use in the batch mode, these probes are readily transportable which enables to perform the sampling for the batch mode remote of the ATR instrument, which is yet another obvious advantage.

Alternatively, a probe according to the invention may be designed as a so-called dynamic probe adapted for a continuous mode of operation with constant throughflow of a test fluid. Such an embodiment is useful for continuous ATR monitoring.

The casing of the probe may be made of any suitable material. During storage the probe may, if desired, be filled with an inert liquid in order to protect in this way the sensing zone of the sensor(s).

During filling, storage and transportation the probes according to the invention used in the batch mode are preferably capped.

For the preparation of an optical fiber sensor according to the invention, an unclad optical fiber is first produced by drawing a preform in a drawing tower as known per se. Thereafter the fiber is cut into pieces of desired lengths and each piece is or alternatively a bundle of pieces are put in a suitably designed heat-stretching device. In a preferred embodiment such heat-stretching device comprises two aligned holders spaced from each other to form a gap at which the fiber is or the fibers are exposed. The end portions of the fibers are attached to the holders and two equal weights are suspended therefrom. The exposed central region of the fiber or fiber bundle is then heated whereby it is softened and stretched in consequence of the pulling action of the two weights. In the course of such stretching the exposed part of each fiber forms into two frustoconical portions which merge at their frustrums, while the outer, unexposed cylindrical portions remain with the original diameter. The device also has stops so adjusted that they arrest the weights when the two merging frustoconical portions are fully developed so as to prevent any undue elongation of the zone of merger between the frustrums thereof.

The sensitivity of the sensor is determined by the elongation of the fiber from which it was made; the more elongated it is, the smaller the diameter of the connecting zone between the cones and the larger the sensitivity.

Upon completion of this sensor shaping operation the fiber(s) is or are cut to size to yield the desired sensor(s), and the sensor(s) is or are mounted into a tubular holder that is to serve as casing of the probe and is or are properly centered and secured therein. Thereafter the two ends of each sensor are polished as known per se.

DESCRIPTION OF THE DRAWINGS

For better understanding the invention will now be described, by way of example only, with reference to the annexed drawings, it being understood that the invention is not restricted thereto. In the drawings.

DETAILED DESCRIPTION OF THE INVENTION

Figure 1:
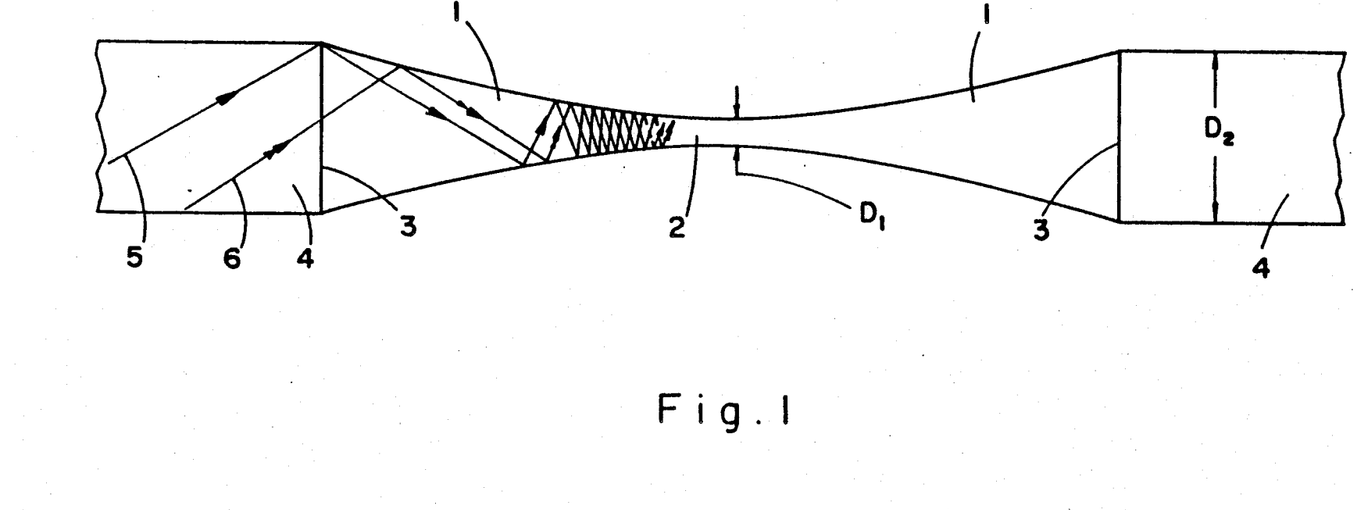
FIG. 1 is an elevation of a sensor for use in a probe according to the invention also showing diagrammatically the increase of the number of reflections per unit length as the diameter decreases in the sensing zone.

FIG. 1 shows an optical fiber sensor used in probes according to the invention. As shown the sensing zone of the sensor comprises two conical portions 1 whose frustrums merge at 2. The distal bases 3 of the conical portions 1 merge into cylindrical fiber portions 4. The diameter D1 of the minimum diameter region 2 of the merger zone is much smaller than the diameter D2 of cylindrical portions 4.

It should be noted here that FIG. 1 and also the following Figures are not drawn to scale and that actually D2/D1 may be significantly larger than shown in the drawings.

In FIG. 1 the manner in which the conical portions 1 on the light intake side increase the number of reflections per unit length is shown diagrammatically by means of notional light rays 5 and 6. It is clearly seen that the distance between the reflection points of these two rays at the fiber surface diminishes gradually from the large diameter cylindrical portion 4 via the conical portion 1 and is at its smallest within the minimum diameter region 2. In other words, in the conical portion 1 the number of reflections per unit length is much larger than in the large diameter cylindrical portion 4.

In use, the two conical portions 1 of a sensor of the kind shown in FIG. 1, are in contact with a test medium and an evanescent lightwave propagates at the test medium/sensor interface. The intensity of the interaction between the evanescent light wave and the surrounding medium is directly proportional to the diameter ratio D2/D1 and to the shape of the two conical portions 1. The critical angle increases with the difference between the refraction indices of the sensor and test medium and consequently sensors with a high refraction index are, as a rule, preferred, e.g. such as are made of chalcogenic glass. Subject to that preference, it is desirable to design a sensor in a probe according to the invention in such a way that the merger region 2 is as thin as practically possible.

Figure 2:
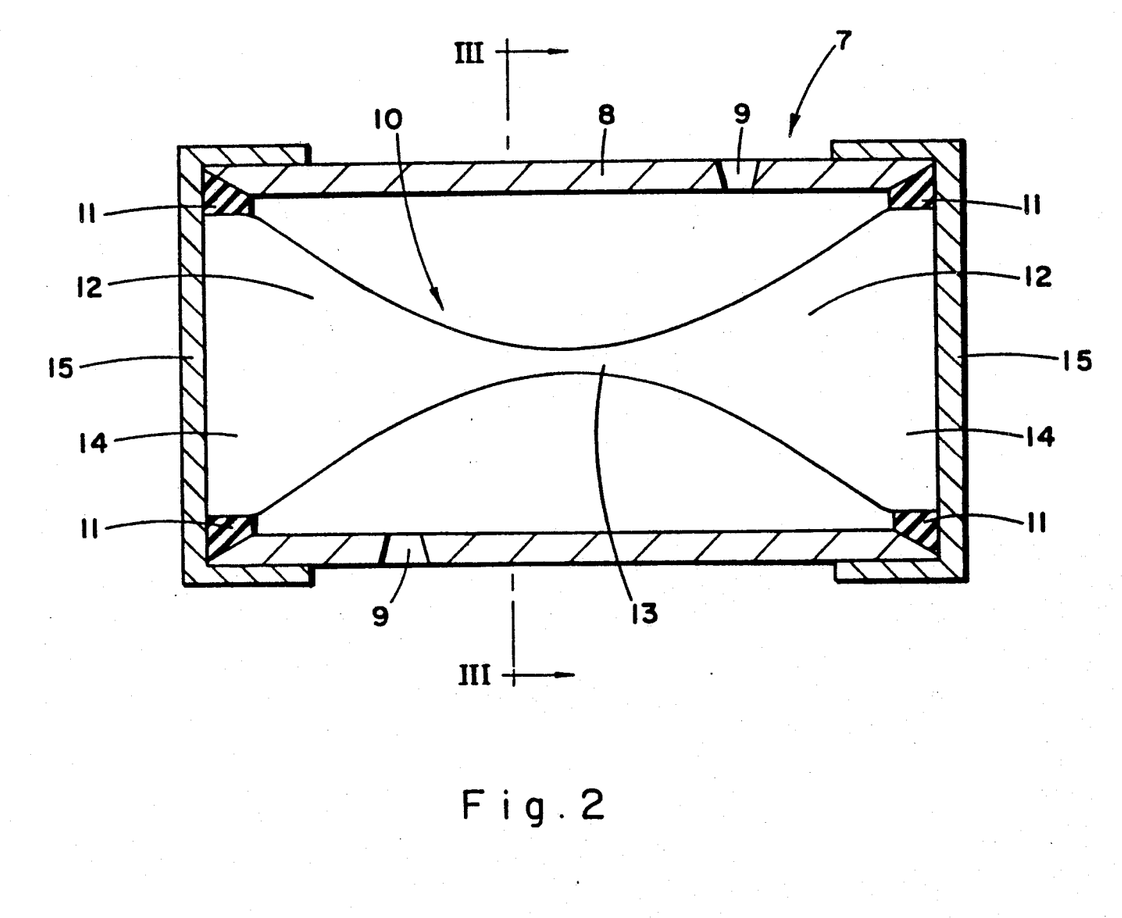
FIG. 2 is an axial section of a probe according to the invention with a single sensor.
Figure 3:
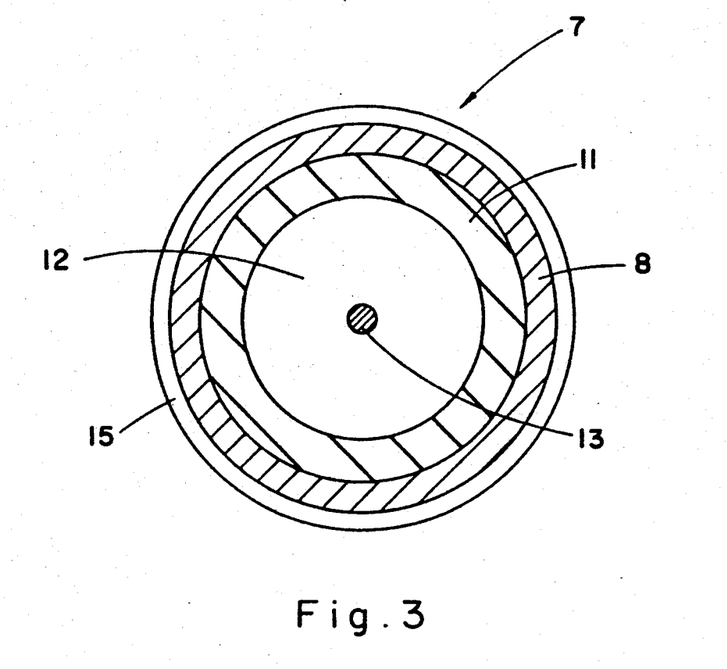
FIG. 3 is a cross-section along the line III—III of FIG. 2.

A typical example of a probe according to the invention for use in a batch mode of operation and having a single fiber sensor is illustrated in FIGS. 2 and 3. As shown, a probe 7 comprises a tubular casing 8 of circular cross-sectional shape. Casing 8 comprises two sealable openings 9 for the introduction and withdrawal of a sample medium. Where the probe is a so-called static probe serving for batch measurement, one single opening 9 may be sufficient.

An optical fiber probe 10 is held within two annular bodies 11 having a tapering cross-sectional shape and made of light blocking material. The shape of the sensor 10 is similar to that shown in FIG. 1 and it comprises two conical portions 12 whose frustrums are joined at 13. The two conical portions 12 merge into cylindrical portions 14. The end of each portion 14 is suitably polished as known per se and during filling, storage and transportation they are protected by means of caps 15.

A probe according to the invention for use in a continuous mode of operation is in principle of similar design with the openings 9, however, being preferably replaced by the inlet and outlet tubes.

Figure 4:
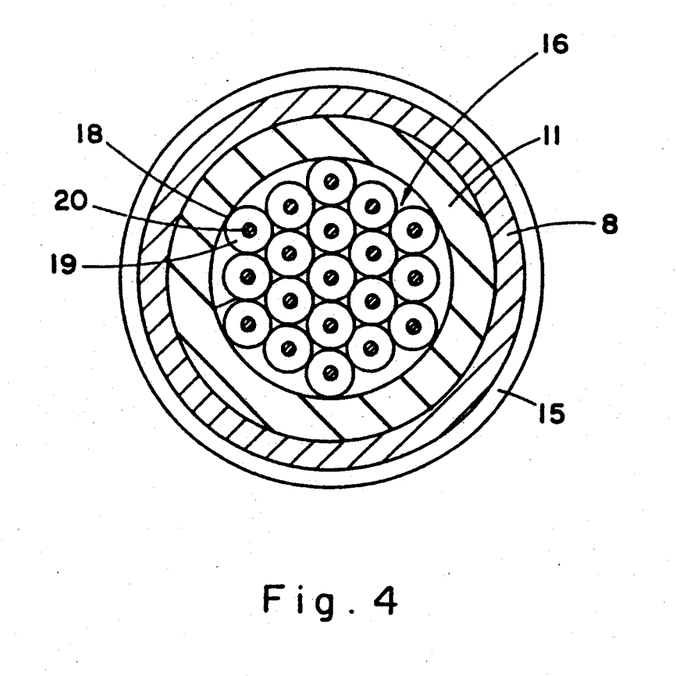
FIG. 4 is a cross-section of a probe according to the invention with a bundle of sensors.

The probe according to the invention shown in cross-section in FIG. 4 is essentially similar to that of FIGS. 2 and 3 with the single fiber sensor being however replaced here by a bundle of sensors, similar components being designated with the same numerals. As shown, the single fiber sensor 10 of FIGS. 2 and 3 is here replaced by a bundle 16 comprising a plurality of individual fibers 18 each having two conical portions 19 (only one being shown in FIG. 4) joined at 20 and each merging into a large diameter cylindrical portion (not shown).

Figure 5:
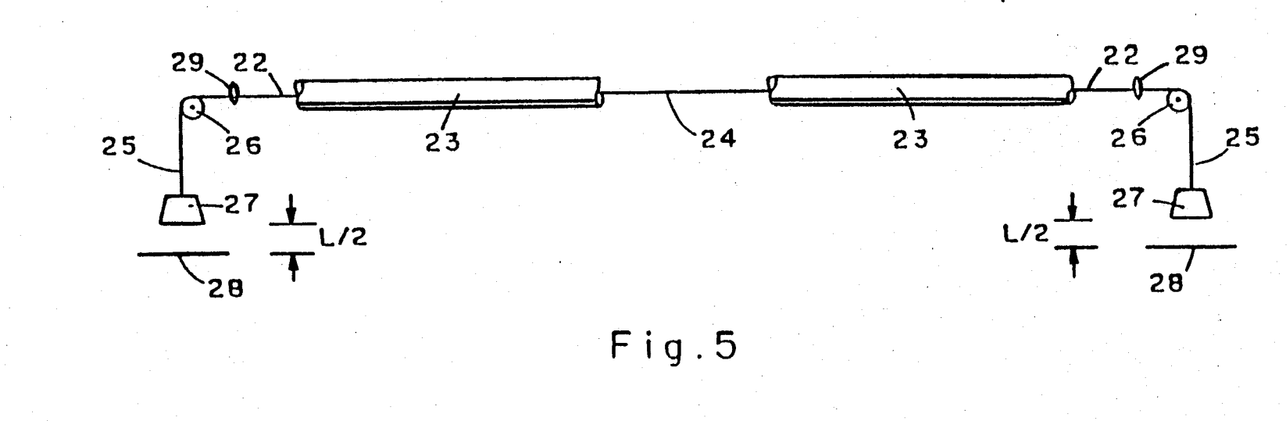
FIG. 5 is a diagrammatic illustration of the production of an optical fiber sensor for a probe according to the invention.

The preparation of a probe with an optical fiber sensor according to the present invention is illustrated diagrammatically in FIG. 5. As shown, an optical fiber piece 22 of suitable length and diameter (50-1000μ) is enclosed within two aligned holders 23 separated by a gap 24. At the two ends of the optical fiber 22 there are attached at 29 strings 25 each of which is supported by a pulley 26 and from each of which there is suspended a weight 27, the two weights 27 being exactly equal.

Underneath weights 27 there are provided stops 28 which are removed from the initail positions of the weight by a distance L/2 where L is the designed length increase of the finished sensor as compared to the length of the starting piece of fiber.

The exposed portion of fiber 22 stretching across gap 24 is heated whereupon that portion softens and stretches with a concomitant reduction of its diameter and the formation of conical portions joined at their frustrums flanked by unstretched, large diameter cylindrical portions of fiber 22. This stretching operation continues until weights 27 are arrested by stops 28 whereupon the heating is interrupted. The product, shaped fiber is then cut to size and shifted into one of the holder tubes 23 that serves as casing in the finished probe according to the invention. Alternatively, the so-formed sections which serve as sensors may be transferred to another holder. The ends of the sensor may then be glued and polished as known per se.

The preparation of a probe with a bundle of discrete sensors is essentially similar.

Figure 6:
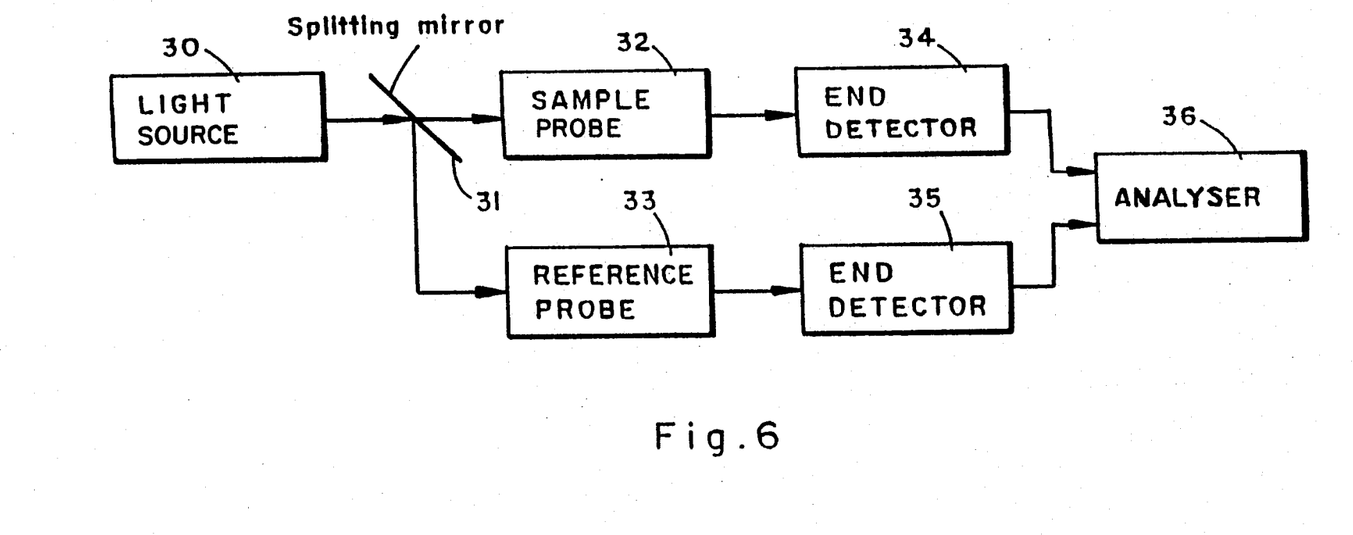
FIG. 6 is a block diagram of an IR spectrometer operating by the ATR method in accordance with the invention.

FIG. 6 is a block diagram of one embodiment of an ATR assembly for recording an IR spectrum with the use of a probe according to the invention. As shown, the spectrometer asembly comprises a light source 30, a splitting mirror 31, a sample probe 32, a reference probe 33, end detectors 34 and 35 and an analyser 36. In operation IR light emanating from light source 30 is split by splitting mirror 31 whereby two rays are created, one which passes through sample probe 32 and the other which passes through reference probe 33. End detectors 34 and 35 detect the modulations of the evanescent light emanating from the sample probe 32 and the reference probe 33, respectively, and the analyser 36 compares the signals produced by the detectors to give a qualitative spectrum and /or an indication of sample concentration.

Instead of employin a splitting mirror 31 it is also possible to connect the sensors of each of the sample probe 32 and reference probe 33 directly to the light source 30.

A COMPARATIVE EXAMPLE

In a first experiment the IR spectrum of a single paraffin drop measuring 0.2 mm was recorded, using a probe according to the invention having a single optical fiber sensor made of $As_2Se_3$ chalcogenic glass and having a refractive index of 2.77. The configuration of the sensor was similar to that shown in FIG. 1 with the sensing zone being 2 cm long and having a diameter of $20\mu$ while the diameter of the flanking cylindrical portions was $500\mu$. Due to its size the paraffin drop was thus in contact with only a small portion of the sensing zone.

Figure 7:
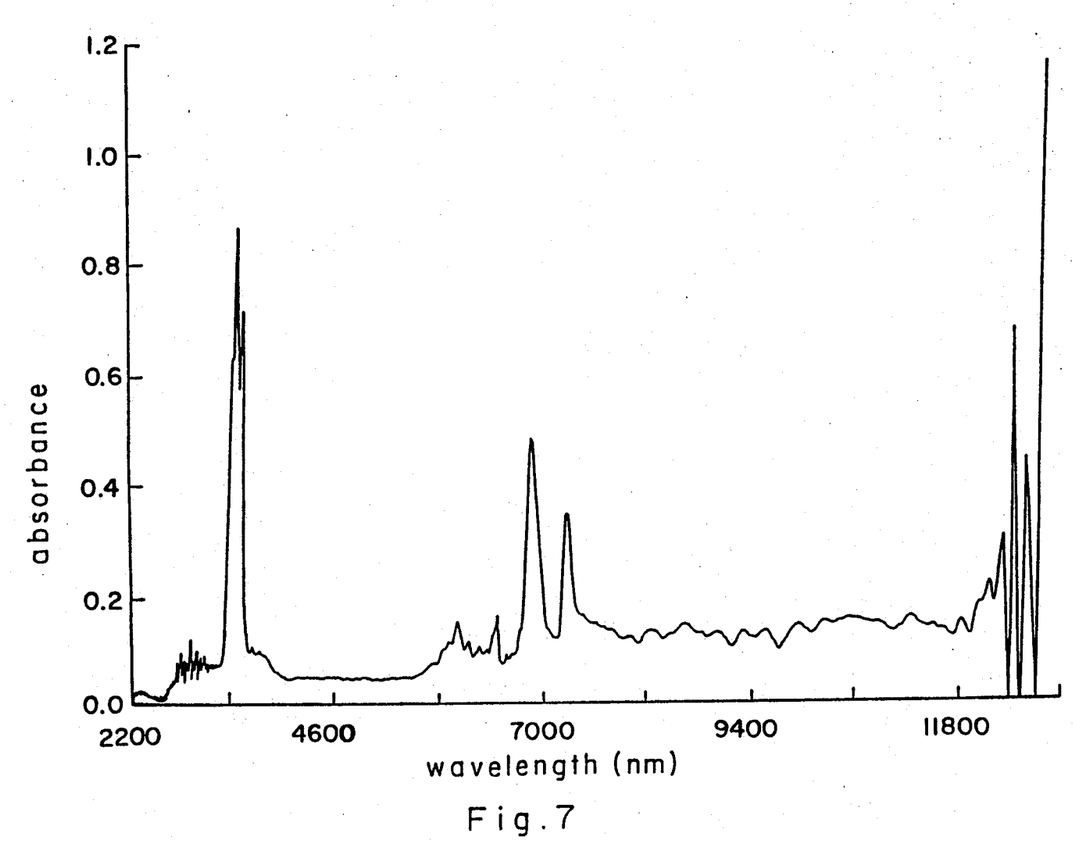
FIG. 7 is an infrared absorption spectrum of paraffin in a probe with a single sensor according to the invention.
Figure 8:
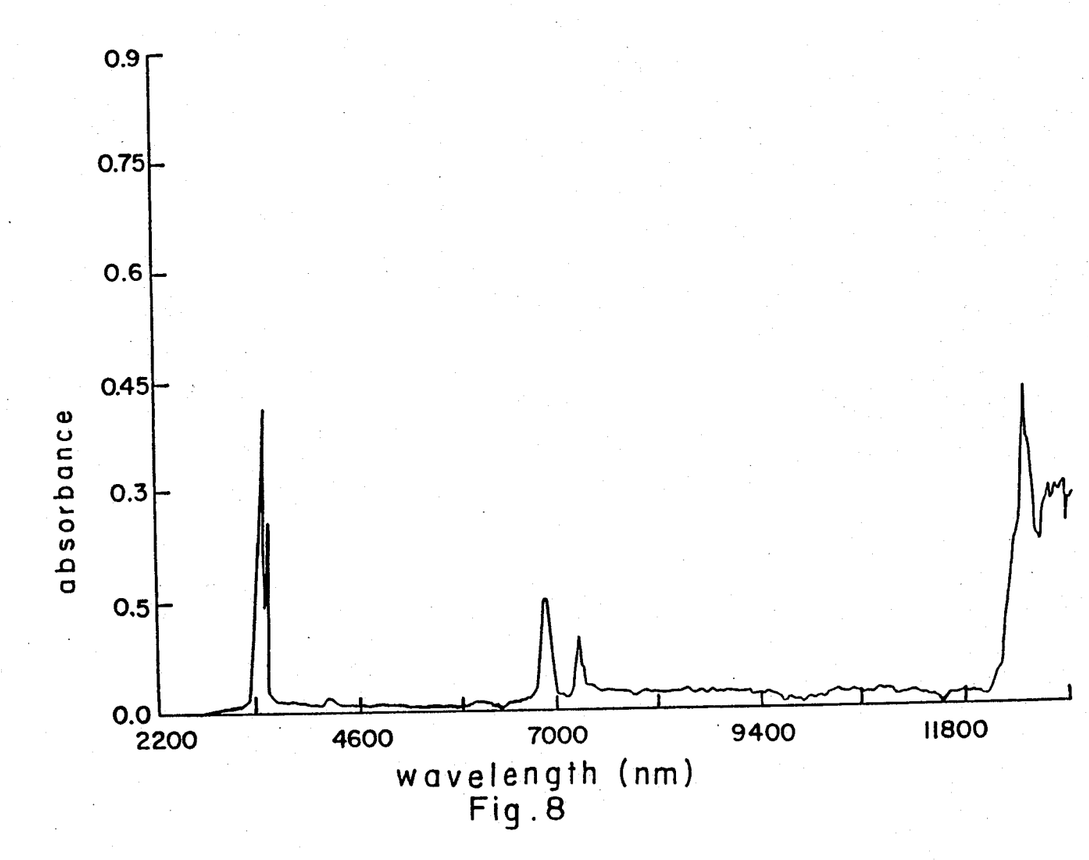
FIG. 8 is an infrared absorption spectrum of paraffin using a prior art probe with a single sensor comprising however a straight optical fiber.

In a second experiment a large size conventional probe was used with a single staight, untapered optical fiber sensor of the same chalcogenic glass, $50\mu$ diameter and having a sensing zone of 20 cm length. The quantity of paraffin in the second experiment was much larger so as to surround the entire length of the optical fiber sensor. In both experiments a Nicolet FTIR spectrometer was used with a reflective optical system for concentrating the light on the sensor. The light emerging from the sensor was measured by external MCT detector that was directly connected to thee analyser. FIG. 7 shows a tracing of an IR spectrum recorded in the first experiment and FIG. 8 shows a tracing of an IR spectrum recorded in the second experiment. By comparing these two tracings it is evident that the sensitivity and resolution power achieved in accordance with the invention is significantly higher than those achieved with a prior art probe. In fact, when comparing the lengths of the contact area of fluid and the sensing zone in the experiment with the probe according to the invention which was about 0.2 mm, with the length of the contact area in the experiment with the conventional straight probe which was equal to the length of the probe, i.e. 20 cm (in that experiment the entire sensor was in contact with the paraffin), it can be shown that the sensitivity of a probe according to the invention is about 2000 fold of that of a conventional optical fiber probe.

It is important to note that in both experiments the diameter of the intake part of the fiber was $500\mu$ and that the concentrating optics was the same. The amplification factor of the double-cone probe according to the invention is thus demonstrated.

We claim:

1. In a method of performing a spectroscopic measurement by the Attenuated Total Reflection technique, comprising providing a tubular probe for holding a substrate medium, and fitting within said probe at least one optical fiber sensor having an unclad sensing zone and light intake and emitting ends, the improvement comprising said unclad sensing zone of each sensor including two frustoconical portions merging at their frustrums.

2. The method of claim 1, comprising using a probe in which the base of each frustoconical portion of each sensor merges into an outer cylindrical portion having the same diameter as the base.

3. The method of claim 2, comprising the step of using a probe having a single sensor.

4. The method of claim 2, comprising the step of using a probe with a bundle of discrete sensors.

5. The method of claim 1, comprising using a probe having a single sensor.

6. The method of claim 1, comprising using a probe with a bundle of discrete sensors.

7. The method claim 1 for the performance of spectroscopic measurements with light in any one of the ultraviolet, visible and near-infrared light regions, wherein a probe is used in which each sensor is made of silica or fluoride based glass fiber.

8. The method according to claim 1 for the performance of spectroscopic measurements with light in the far infrared light region, wherein a probe is used in which each sensor is made of a chalcogenic compound based glass fiber.

9. A probe for sensing the performance of a spectroscopic measurement by the Attenuated Total Reflection technique, the probe comprising a tubular casing including means for holding a substrate medium and being fitted with at least one optical fiber sensor inserted therein and having an unclad sensing zone, a light intake end and a light emitting end, said unclad sensing zone of each sensor comprising two identical frustoconical portions merging at their frustrums.

10. The probe of claim 9, wherein the bases of the frustoconical portions of the sensor merge into an outer cylindrical portions having the same diameter as the bases.

11. The probe of claim 10, wherein the cylindrical casing has a circular cross-sectional shape.

12. The probe of claim 10, wherein the cylindrical casing has a polygonal cross-sectional shape.

13. The probe of claim 10, comprising a single sensor.

14. The probe of claim 10, comprising a bundle of discrete sensors.

15. The probe of claim 9, wherein the cylindrical casing has a circular cross-sectional shape.

16. The probe of claim 15, comprising a single sensor.

17. The probe of claim 15, comprising a bundle of discrete sensors.

18. The probe of claim 9, wherein the cylindrical casing has a polygonal cross-sectional shape.

19. The probe of claim 9, comprising a single sensor.

20. The probe of claim 9, comprising a bundle of discrete sensors.

21. The probe of claim 9, wherein each sensor is made of the material selected from the group consisting of silica and fluoride based glass fiber.

22. A probe according to claim 9, wherein each sensor is made of chalcogenic compound based glass fiber.

23. A sensor for use in spectroscopic measurement by the attenuated total reflection technique, being an optical fiber comprising an unclad sensing zone having two frustoconical portions merging at their frustrums.

24. The sensor of claim 23 made of silica or fluoride based glass.

25. The sensor of claim 23 made of chalcogenic compound based glass.

* * * * *